(12) United States Patent
Ascher et al.

(10) Patent No.: US 8,197,945 B2
(45) Date of Patent: Jun. 12, 2012

(54) MECHANICAL PIECE WITH IMPROVED DEFORMABILITY

(75) Inventors: Gilles Ascher, Paris (FR); Johannes Lammer, Lausanne (FR)

(73) Assignee: Hexacath, Rueil-Malmaison (FR)

( * ) Notice: Subject to any disclaimer, the term of this patent is extended or adjusted under 35 U.S.C. 154(b) by 965 days.

(21) Appl. No.: 11/793,977

(22) PCT Filed: Dec. 5, 2005
(Under 37 CFR 1.47)

(86) PCT No.: PCT/EP2005/056459
§ 371 (c)(1),
(2), (4) Date: Aug. 1, 2008

(87) PCT Pub. No.: WO2006/067031
PCT Pub. Date: Jun. 29, 2006

(65) Prior Publication Data
US 2009/0081450 A1    Mar. 26, 2009

(30) Foreign Application Priority Data
Dec. 24, 2004   (EP) .................................. 04293131

(51) Int. Cl.
*A61F 2/04*      (2006.01)
*B32B 15/04*     (2006.01)
(52) U.S. Cl. .................. 428/457; 428/469; 623/23.7
(58) Field of Classification Search .................. None
See application file for complete search history.

(56) References Cited

U.S. PATENT DOCUMENTS

| | | | | |
|---|---|---|---|---|
| 5,652,464 A * | 7/1997 | Liao et al. | ...... | 257/751 |
| 5,972,128 A * | 10/1999 | Miwa | ...... | 148/321 |
| 6,099,561 A | 8/2000 | Alt | | |
| 6,150,720 A * | 11/2000 | Yamaha et al. | ...... | 257/751 |
| 6,291,344 B1 * | 9/2001 | Liao et al. | ...... | 438/653 |
| 6,576,482 B1 * | 6/2003 | Aggarwal et al. | ...... | 438/3 |
| 7,388,042 B2 * | 6/2008 | Yadav et al. | ...... | 523/200 |
| 7,391,018 B2 * | 6/2008 | Niu et al. | ...... | 250/288 |
| 2001/0036530 A1 | 11/2001 | Noda et al. | | |
| 2003/0047808 A1 * | 3/2003 | Agarwal | ...... | 257/751 |
| 2003/0207028 A1 * | 11/2003 | Boire et al. | ...... | 427/226 |
| 2006/0113578 A1 * | 6/2006 | Chung et al. | ...... | 257/303 |
| 2008/0082162 A1 * | 4/2008 | Boismier et al. | ...... | 623/1.38 |
| 2009/0018645 A1 * | 1/2009 | Cambronne et al. | ...... | 623/1.34 |
| 2009/0053491 A1 * | 2/2009 | Loboda et al. | ...... | 428/216 |
| 2010/0303722 A1 * | 12/2010 | Jin et al. | ...... | 424/9.1 |

FOREIGN PATENT DOCUMENTS

| | | |
|---|---|---|
| GB | 2 385 062 | 8/2003 |
| WO | WO2004/030578 | 4/2004 |

* cited by examiner

*Primary Examiner* — Jennifer McNeil
*Assistant Examiner* — Jason Savage
(74) *Attorney, Agent, or Firm* — Clark & Brody

(57) ABSTRACT

The invention relates to a mechanical piece having a structure comprising a substrate (1) and at least one surface coating layer (3) of nanometric thickness, for improving mechanical resistance, characterized in that it comprises between the substrate and the surface coating layer an essentially non ceramic, non porous adhesion layer of nanometric size; and said surface coating layer is an essentially non porous barrier layer (2) consisting essentially of an essentially stoechiometric titanium nitride layer.

13 Claims, 1 Drawing Sheet

MECHANICAL PIECE WITH IMPROVED DEFORMABILITY

The present invention relates to a mechanical piece comprising several coating layers of nanometric thickness, having a great aptitude to plastic deformation and a prolongated fatigue resistance.

STATE OF THE ART

Mechanical pieces, like stents, have been used since a long time for different purposes, and notably as an implant or insert within the body of a live being, notably for repairing blood vessels having different defects like a narrowing path or having suffered of thrombosis.

It is known from document U.S. Pat. No. 6,110,204 a biocompatible implant coated with at least one layer of a coating material comprising one of several metals of group IVA of the periodic table, of nitrogen (N), and oxygen (O), in a ratio of 1:(0.1 to 1.7):(0.1 to 1.7) such as it results into a material having formula $MN_xO_y$, wherein x, y,=0.1 to 1.7 (see claim 1, column 7). This coating layer is compulsory porous.

This coating, which comprises a combination of a metal, nitrogen and oxygen does constitute a ceramic, which is well-known to those skilled in the art not to be capable of any plastic deformation.

According to another embodiment foreseen in claim 2, this layer of coating material may also comprise other chemical compounds, namely mixtures of $MN_x$, $Mo_x$, phases of Magnelli of the system $M-O(MnO(2n-1))$; $MO_2$, $M_2N$.

According to another particular embodiment, foreseen in claim 3, the coating material may contain minor amounts of a carbon compound and of a metal of the same group IVA.

According to a further particular embodiment, the thickness of the layer of coating material on the substrate is ranging between 3 nanometers and 3 millimeters.

According to a further particular embodiment, the coating layer is coated with at least one additional thin layer of one of several oxides selected from the group consisting of $SiO_2$, $TiO_2$, $ZrO_2$, $HfO_2$, $AlO_2$, $Y_2O_3$, and niobium oxides, molybdenum oxides, tungsten oxides, and tantalum oxides (claim 12).

It can also be further foreseen a thin additional layer of a metal or of a semi conductor metal introduced between the substrate and the coating (claim 13).

It is also known by the Russian article made by PANTCHOHA et al. published in the Russian Revue "Stomatologiya" (1986), 65(5) 51-3, an implant made of a stainless steel type 316L coated by a single ceramic coating layer of TiN; TiO; Ti(NO) and ZrN. The authors concluded with a biocompatibility of these so-coated stents implanted in the body of rats.

Purposes of the Invention

A main goal of the invention is to provide industrial mechanical pieces submitted to strong superficial solicitations, and which need a great aptitude to plastic deformation together with a prolongated fatigue resistance.

Another main goal of the invention is to provide biocompatible mechanical pieces which may be used as implant within the body of a live being, in particular of an animal or of a human being, having a great aptitude to plastic deformation and a prolongated fatigue resistance.

SUMMARY OF THE INVENTION

The invention enables to solve all of these technical programs in a manner which is simple, reliable and reproducible, usable at the industrial and medical scale.

According to a first aspect of the invention, it is provided a mechanical piece having a structure comprising a substrate and one ceramic coating layer of nanometric thickness, for improving mechanical resistance, characterized in that it comprises, between the substrate and the ceramic coating layer, an essentially non porous metallic adhesion layer of nanometric size providing plastic deformability to the ceramic layer.

According to the invention, by the terms "non porous layer" or "essentially non porous layer", it is meant the layer does not essentially comprise pores, namely in practice the percentage of pores is as low as possible, ideally of 0%, according to a method of deposition which does not provide the formation of pores in the coating layer. The presence of pores has to be avoided according to the present invention, since the pores and their walls can be the source of cracks.

One skilled in the art will understand that the essentially non porous coating layer provides the lowest coefficient of friction versus all metallic compounds and is particularly useful in case of tribological applications, namely when there are relatively movable parts into friction contact one with the other.

According to an advantageous invention embodiment, said mechanical piece, when the substrate does not comprise, or is not constituted of, titanium, further comprises an essentially non porous barrier layer of nanometric size comprising a metal preferably selected from chromium, or any metal selected from group IV A of the periodic system or table.

According to another advantageous invention embodiment, said metallic adhesion layer comprises a metal selected from chromium metal, a chromium alloy, a titanium metal, a titanium alloy, or a mixture thereof.

According to a further advantageous invention embodiment, said mechanical piece further comprises, after said chromium metal or chromium compound layer, a nanometric essentially non porous transient diffusion layer of a metal or a metal compound of group IV A and/or V A of the periodic table, notably selected from the group consisting of titanium, zirconium, hafnium, vanadium, niobium, tantalum.

According to a further advantageous invention embodiment, said mechanical piece is characterized in that it comprises an essentially non porous barrier upper coating layer of nanometric sizes of essentially stoechiometric titanium nitride.

According to another advantageous invention embodiment, said substrate is coated with an adhesion layer of nanometric size, essentially non porous, of essentially pure titanium, followed by a surface coating layer consisting of an essentially non porous coating barrier layer of nanometric size of essentially stoechiometric titanium nitride.

According to a further advantageous invention embodiment, said mechanical piece further comprises, over the coating barrier layer of titanium nitride, a further surface layer of nanometric size, essentially non porous, essentially consisting of titanium oxide nitride.

According to another advantageous invention variant embodiment, said mechanical piece further comprises, over the ceramic barrier layer, a second essentially pure titanium nanometric, non porous coating layer.

According to another advantageous invention variant embodiment said mechanical piece further comprises, over the second essentially pure titanium nanometric layer, a second essentially stoechiometric titanium nitride nanometric, non porous, coating layer.

According to another advantageous invention variant embodiment said mechanical piece further comprises, over the second essentially stoechiometric titanium nitride nanometric coating layer, a second upper layer essentially consisting of a titanium oxinitride, non porous coating layer.

According to a further advantageous invention variant embodiment, each titanium oxinitride coating layer has a chemical formula TiNxOy, wherein x ranges between about 0.7 and about 1; and y is 1−x.

According to another advantageous invention variant embodiment, said mechanical piece further comprises, between each coating layer, a transient diffusion layer of nanometric size, essentially non porous, of a solid solution of at least one metal of the preceding layer and of at least one metal of the following layer.

According to a further particular invention variant embodiment, the mechanical piece is characterized in that the thickness of each nanometric coating layer is at the minimum equal to about 10 nm. In addition, the preferred maximum thickness of each of these coating layers is of about 40 nm.

Thus, preferably, the thickness of each nanometric layer ranges between about 10 nanometers and 40 nanometers.

A highly preferred thickness for each of these layers is of about 25 nm.

According to another preferred feature, the adhesion layer or the transient diffusion layer has a thickness ranging between 5 and 20%, preferably of about 10%, of the thickness of the coating layer.

According to another advantageous invention embodiment, the substrate is made of a metal or alloy selected from a steel, in particular stainless steel; a titanium or titanium alloy; or a shape memory alloy.

This steel can be according to a first variant a low carbon alloy steel.

According to another variant said steel can be a high carbon alloy steel. By low carbon is meant a steel having less than about 0.05 weight % of carbon.

According to another advantageous invention variant embodiment, on said substrate, it is provided a nanometric, essentially non porous, adhesion layer selected from the group consisting of an essentially pure chromium metal or chromium alloy, and of a titanium metal or titanium alloy, or a successive combination of both.

According to another advantageous invention variant embodiment, said substrate is a plastic substrate, notably selected from the group consisting of a polyester, a polyamide, a polyurethane, a polyethylene, a polytetrafluoroethylene, a polycarbonate. The plastic substrate is preferably a polycarbonate.

According to a further advantageous invention variant embodiment, said mechanical piece is a medical implant. Preferably, the medical implant is selected from the group consisting of a vascular implant, such as a stent, a graft; an orthopaedic implant, such as a knee implant or hip implant.

According to another advantageous invention variant embodiment, said mechanical piece is a mechanical watch regulatory mechanism, in particular an escape mechanism and/or escape time-keeping mechanism.

According to another advantageous invention variant embodiment, in said titanium nitride layer, the proportion in nitrogen is at the maximum stoechiometric, and in particular ranges between 0.7 and 1.

One skilled in the art will understand that, due to the invention, the technical problems previously set forth in the goals of the invention are solved, in a way which is simple, of low-cost, usable at the industrial scale, without limitation to particular forms or shapes of the mechanical pieces sought, which are submitted to a high plastic deformation, or a high fatigue solicitation. The invention allows to combine any mechanical properties of a substrate with the biocompatible advantages of the claimed surface modifications of the invention, thereby increasing versatility and the choice of substrates, including plastics.

It will also be observed that within the scope of the invention, the nanometric coating layers can be implemented according to techniques of depositing layers providing essentially non porous layers well known to one skilled the art. These techniques are for instance the physical-vapor deposition, the chemical-vapor deposition, such as the Activated Reactive Evaporation method (called ARL), the reactive direct current or HF magnetron sputtering method or the Reactive Filtered Arc Plasma Deposition, the thermo-Chemical Vapor Deposition, the Organo-Metallic Thermo-Chemical Vapour Deposition, the Photochemical vapour Deposition, Sol-gel Procedures. The general conditions of working of these methods are well known to the skilled person in this art and will further appear from the description of the examples.

The present invention will be now illustrated by way of examples given only for illustration purpose and which are therefore not intended to limit the scope of the invention. The examples, completed by the drawings, are an integral part of the invention; and any feature, which appears to be novel over any state of the art, is claimed per se in its function and as a general means as is well understood by one skilled in the art.

EXAMPLE 1 OF THE INVENTION

Figure 1:
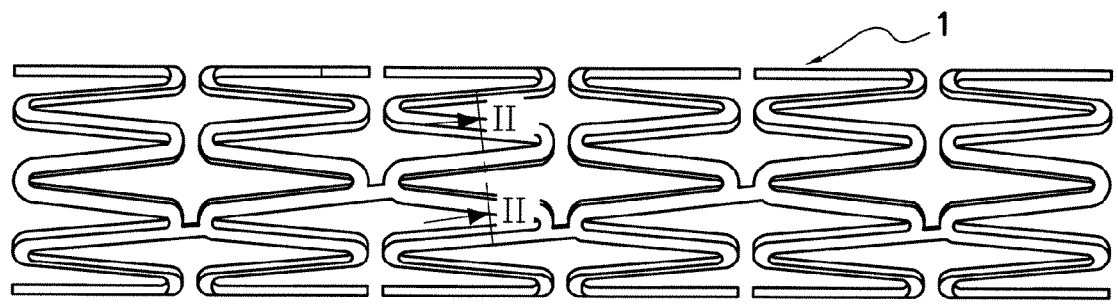
FIG. 1 shows an enlarged photograph of a not deployed biocompatible intraluminal coronary ballooning stent which, according to a first invention embodiment, is covered by three coating layers, as prepared in example 1, shown in the cross-section of FIG. 2.
Figure 2:
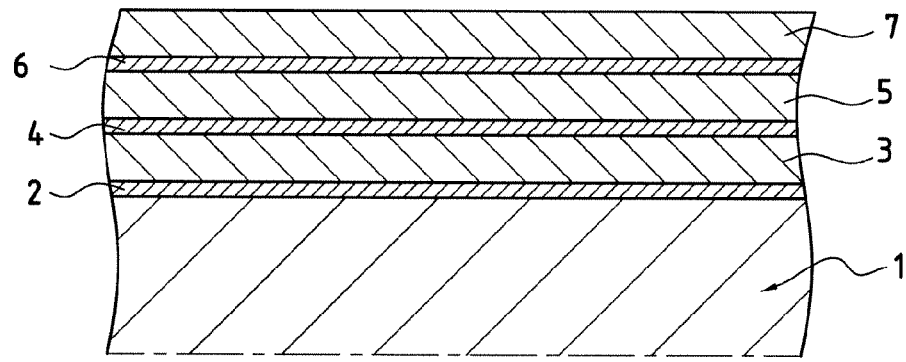
FIG. 2 is a cross-section of a branch of the stent shown in FIG. 1 wherein the three coating layers, as prepared in example 1 are clearly apparent.

A Biocompatible Intraluminal Coronary Ballooning Stent having Improved Mechanical Resistance Comprising THREE Surface Coating Layers A biocompatible stent is prepared, which comprises from bottom to the top, and in reference to FIGS. 1 and 2:

a) a substrate 1, constituting the stent skeleton, usually made from a wire spirally coiled, is here prepared with a stainless steel of medical grade comprising nickel, chromium and low carbon, for instance a stainless steel of the grade material No 1.44.35 as defined in EURONORM equivalent to AISI 316L, for instance having a cross-section of wire of 0.01 mm$^2$, and a stent overall diameter of 1.5 mm under the undeployed state, which can be manufactured, as well known, for instance by laser cutting of a metal tube;

This substrate 1, now representing a stent, is cleaned by Radio-Frequency Magnetron sputtering during 5 minutes at 2.5$^{-2}$ hPa Argon pressure;

b) a first transient diffusion layer 2 serving as an adhesion layer, avoiding or minimizing crack formation and crack propagation, of a solid solution of a metal alloy preferentially selected from titanium or chromium, intermediate with the previous and next metallic coating layer of a thickness of from 2 to about 10 nm, preferably of about 5 nm;

This transient diffusion layer 2 is obtained by increasing the partial pressure of nitrogen from 0 to 16 vol % during a time preferentially of about 1 min 30 sec.

c) a first coating layer 3 of essentially pure titanium having a thickness ranging between 10 nm and 40 nm, most preferably of about 15 nm;

c1) Coating by Using Ratio-frequency Magnetron Sputtering.

the pure titanium layer can be deposited by using ratio-frequency magnetron sputtering at $3.5^{-3}$ hPa Argon, with a cathode power of 6 watts/cm$^2$; 1200 volts; with in this embodiment a RF-bias of 200 volts. These values can be modified of +/−20%. The duration of the coating is of 3 minutes for a layer thickness of 40 nanometres. Accordingly, for a preferred thickness of 15 nanometres, the duration will be of 1 min 30 sec.

c2) Filtered Arc-Coating Method

Similarly, it can used the Filtered Arc-coating method according to which the pure titanium coating is obtained at a pressure of $2^{-4}$ hPa pure Argon with a duration of 1 minute for obtaining a thickness of 40 nanometres.

c3) Low Temperature CVD Coating Method

It can also be used similarly a low temperature CVD method according to which, after the sputter-cleaning, a slow heating is performed up to 480° C. Then, it is introduced the reactive gas measure, namely hydrogen and an organo-metallic titanium compound for obtaining said titanium pure layer at a total pressure of 400 hPa with a partial pressure in hydrogen of 90% and the organo metallic being 10%.

d) a second artificial transition layer 4, serving as a crack propagation barrier, created by a variation of the partial pressures of the reactive gases, comprising a solid solution of a metal alloy intermediate with the previous Titanium and next metallic coating layer, here comprising titanium nitride having a nitrogen content between 0.7 and less than 1, of a thickness ranging between 10 nm and 40 nm, most preferably of about 15 nm.

d1) When using the Radio-Frequency Mangetron sputtering coating method, it is added 16% volume nitrogen to the Argon at the same total pressure. The duration of coating for obtaining said titanium nitride layer is of 8 minutes for 40 nanometres.

e) a second coating ceramic layer 5 of essentially pure titanium nitride, namely wherein the nitrogen content is essentially equal to 1 for one atom of titanium, having a thickness ranging between 10 nm and 40 nm, most preferably of about 15 nm.

When using the radio-frequency magnetron sputtering coating method, to deposit this layer, it is added 16% volume nitrogen to the Argon at the same total pressure. The duration of coating for obtaining said titanium nitride layer is of 8 minutes for 40 nanometres.

Similarly, with the low temperature CVD method, it can be introduced a reactive gas measure comprising hydrogen and ammoniac and an organo metallic of titanium for getting the titanium nitride layer at a total pressure of 400 hPa with a partial pressure of hydrogen 90%, organo metallic titanium 5% and ammoniac 5%.

f) a third transient diffusion layer 6 avoiding or minimizing crack formation and crack propagation comprising a solid solution of a metal alloy intermediate with the previous and next metallic coating layer, here comprising titanium oxinitride having a nitrogen (N) content ranging between 0.7 and less than 1 and an oxygen content equal to 1 —(N) content, of a thickness ranging between 10 nm and 40 nm, most preferably of about 15 nm.

This third transient diffusion layer 6 of titanium oxide nitride can be obtained as follows:

under RF magnetron sputtering method, it is foreseen to get a proportion N/O in the deposit layer of 3/1, (namely about 0.75% nitrogen for about 0.25% oxygen), of a proportion in the partial pressure of N/O of 10/1 with a same total gas pressure of $3.5 \cdot 10^{-3}$ hPa combining Argon+oxygen+nitrogen gases.

The duration of coating is of about 8 minutes for 40 nanometres.

Similarly, it can also be used the filtered arc-coating method under the same relationship of nitrogen and oxygen; the duration of coating is of 3 minutes for a thickness of 40 nanometres.

Similarly, under the low temperature CVD method, the coating is performed at a temperature of 480° C. with introduction of the reactive gas measure comprising hydrogen, organo metallic titanium and ammoniac and oxygen at a total gas pressure of 400 hPa with partial pressures of hydrogen 90%, organo metallic titanium 1.5%, ammoniac 5% and oxygen 0.5%.

g) a third coating layer 7, here constituting the surface layer, of essentially pure titanium oxinitride, namely where the total of nitrogen and oxygen content is essentially equal to 1 for 3 atoms of titanium, having a thickness ranging between 10 nm and 40 nm, most preferably of about 15 nm.

When using the radio-frequency magnetron sputering coating method, to produce this layer, it is added 16% volume nitrogen to the Argon at the same total pressure. The duration of coating for obtaining said titanium nitride layer is of 8 minutes for 40 nanometres.

It can be understood by one skilled in the art that the novelty and unobviousness of the invention lies in the fact that it comprises the use of nanostructured thin non porous layers which by alternating the mechanical properties such as Young's modulus E, then their ultimate tensile stress resistance, provides a ceramic type coating enabling use in many new applications in, so far, inaccessible for ceramic coatings and providing surface integrity in spite of extensive elastic and plastic deformations.

By way of example only, on an average stent of 16 mm length, total surface, inside (lumen) and periphery of 4 mm2, it is deposited the equivalent of 4 micrograms of relevant material for a layer of 1 micrometer thickness (+/−10%), thus according to the actual stent the equivalent mass.

The invention enables a plastic deformation of at least 200% and a conserving of its mechanical integrity, even after 380 millions of alternative solicitations as shown in example 2.

The present stent, illustrated in FIGS. 1 and 2, has been submitted to a simulated lifetime test according to the relevant legislation and after a service time of 10 years equivalent, no degradation of the stent could be observed.

The coating would be preferentially performed by reactive filtered Arc-ion beam deposition.

EXAMPLE 2 OF THE INVENTION

Figure 3:
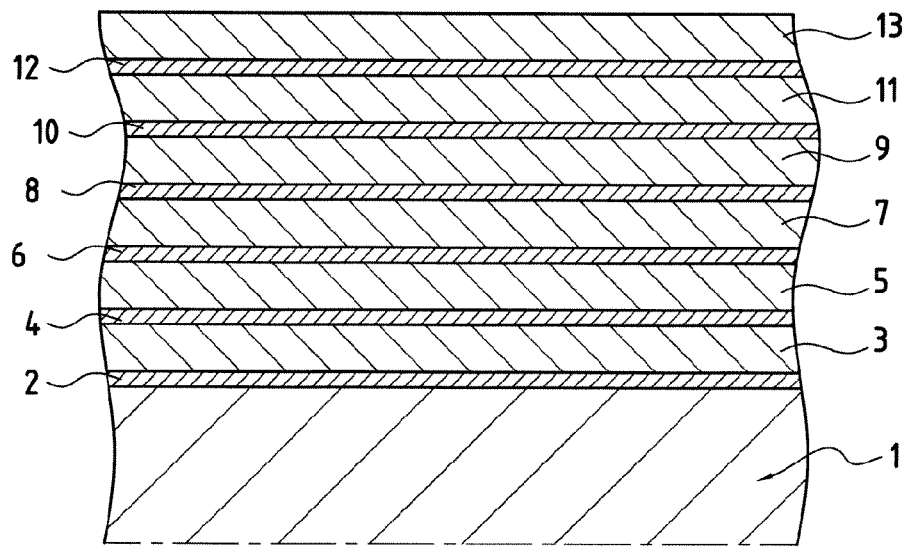
FIG. 3 is a cross-section of a branch of a stent similar to that shown in FIG. 1 which, according to a second embodiment, is covered by six coating layers formed by two sets of successive three essentially identical layers.

A Biocompatible Intraluminal Coronary Ballooning Stent having Improved Mechanical Resistance Comprising SIX Surface Coating Layers A second embodiment of stent is prepared with SIX coating layers, as shown in FIG. 3, for instance starting from the THREE coating layers stent as obtained in example 1, by using the same coating method for the same type of layer as described in example 1, as follows;

h) preferentially a fourth transient diffusion layer 8, avoiding or minimizing crack formation and crack propagation, is deposited on the third surface coating layer 7, comprising a solid solution of a metal alloy intermediate with the previous and next metallic coating layer, here comprising titanium oxinitride having a nitrogen of the of the (N) content ranging between 0.7 and less than 1 and an oxygen content equal to 1−N content, of a thickness ranging between 10 nm and 40 nm, most preferably of about 15 nm.

i) a fourth coating layer 9 essentially identical to the first surface coating layer 3, thus of essentially pure titanium, having a thickness ranging between 10 nm and 40 nm, most preferably of about 15 nm.

j) preferentially a fifth transient diffusion layer 10, avoiding or minimizing crack formation and crack propagation, essentially identical to the second transient diffusion layer 4, thus comprising a solid solution of a metal alloy intermediate with the previous and next metallic coating layer, here comprising titanium nitride having a nitrogen content ranging between 0.7 and less than 1, of a thickness ranging between 10 nm and 40 nm, most preferably of about 15 nm.

k) a fifth coating layer 11, essentially identical to the second surface coating layer 5, thus of essentially pure titanium nitride, namely where in the nitrogen content is essentially equal to 1 for one atom of titanium, having a thickness ranging between 10 nm and 40 nm, most preferably of about 15 nm.

l) preferentially a sixth transient diffusion layer 12, avoiding or minimizing crack formation and crack propagation, essentially identical to the third diffusion layer 6, thus comprising a solid solution of a metal alloy intermediate with the previous and next metallic coating layer, here comprising titanium oxinitride having a nitrogen of the of the (N) content ranging between 0.7 and less than 1 and an oxygen content equal to 1−N content, of a thickness ranging between 10 nm and 40 nm, most preferably of about 15 nm.

m) a sixth surface coating layer 13, essentially identical to the third surface coating layer 7, thus of essentially pure titanium oxinitride, namely where the total of nitrogen and oxygen content is essentially equal to 1 for 3 atoms of titanium, having a thickness ranging between 10 nm and 40 nm, most preferably of about 15 nm.

Such a six-coating layers stent has extraordinary mechanical properties, notably an exceptionally good aptitude to plastic deformation together with a highly prolonged fatigue resistance.

Fatigue Mechanical Tests

The stent, which has been obtained with six coating layers and six adhesive or transient layers, has been submitted to a mechanical fatigue test as follows:

the stent is positioned on a balloon of a catheter, thereby constituting an endoprosthesis, which is positioned in a tube made in plastic estane, which is transparent, and mimics the artery in an internal chamber of a mechanical test module.

The estane tube is by far more elastic than the stent, so that it is the periphery of the stent, which resists to the difference of pressure, which is imposed between the internal chamber and the external chamber of the module, the estanet tube serving only as an interface.

To provide fatigue stresses, cycles of pressure and lack of pressure are applied, when the stent is in the deployed state against the internal wall of the estane tube, by injecting a settable air volume through a pneumatic pump into the higher chamber of the reservoir. The pressure is released by putting the chamber into contact with the atmosphere via a calibrated orifice.

Accordingly, the admission of the air fluid volume in the higher chamber provides an increase of pressure within the reservoir and the module external chamber, thereby creating a difference of pressure between the internal and the external chambers of the module. Of course, the communication with the atmosphere of the higher chamber of the reservoir enables coming back to atmospheric pressure of the external chamber of the module.

The Mechanical Tests Themselves

For performing the mechanical tests, it has been prepared six identical stents according to the present example 2, which have been put on six endoprostheses in the module, the stent being positioned externally onto inflatable balloons as it is well-known in the endoprosthesis art.

The balloons are inflated to deploy the stents at a nominal pressure of 6 bars.

Then, the diameter of the six deployed stents is measured at first in the non-constrained state (0 pressure) and then under a fatigue pressure of 40 mm mercury, which is that corresponding in vivo to the blood pressure. A first measure is taken as 0 cycle and then every 38 millions of cycles (corresponding to an in vivo one year life). The fatigue tests are stopped after 380 millions of cycles have been performed.

When stopping the fatigue tests, it is measured the diameter of the six endoprostheses having been submitted to the fatigue tests both under the non-constrained state and under a mechanical fatigue pressure of 40 mm mercury Then, the stents are withdrawn from the fatigue machine.

There is performed a general examination of the six endoprosthesis according to the invention as obtained according to the procedure of example 2 and they are compared to two endoprosthesis having been undeployed and serving as comparative stents.

It is performed the examination with an electronic scanning microscope of the state of the surface of the all of the endoprosthesis, the two endoprosthesis serving as reference being examined under the undeployed state and after deployment at the nominal pressure of 6 bars.

The mechanical fatigue tests are reported in tables 1 and 2 herebelow respectively.

In table 1, it has been measured the diameter of the stents deployed under a pressure of 6 bars, but when not submitted to any constraint or pressure after the number of cycles indicated.

On the other hand, in table 2, it has been reported the diameter of the stents measured when they are submitted in the deployed state under an external pressure of 40 mm Hg, after the number of cycles indicated.

TABLE I

Diametre under a non-constrained state of six different deployed stents as obtained in example 2

| Number of cycles (millions) | Stent #1 | Stent #2 | Stent #3 | Stent #4 | Stent #5 | Stent #6 |
|---|---|---|---|---|---|---|
| 0 | 2.99 | 2.98 | 3.04 | 3.02 | 3.02 | 2.98 |
| 38 | 3.02 | 3.01 | 2.98 | 2.99 | 2.97 | 2.98 |
| 76 | 3.08 | 3.00 | 3.02 | 3.02 | 2.94 | 2.99 |
| 114 | 3.04 | 3.03 | 3.01 | 3.01 | 2.98 | 3.00 |
| 152 | 3.02 | 3.01 | 3.03 | 3.03 | 2.99 | 3.01 |
| 190 | 3.01 | 2.97 | 3.03 | 3.02 | 3.00 | 3.03 |
| 228 | 3.00 | 2.98 | 3.01 | 3.00 | 3.01 | 2.99 |
| 266 | 3.00 | 2.99 | 3.03 | 3.02 | 3.01 | 3.00 |

TABLE I-continued

Diametre under a non-constrained state of six different deployed stents as obtained in example 2

| Number of cycles (millions) | Stent #1 | Stent #2 | Stent #3 | Stent #4 | Stent #5 | Stent #6 |
|---|---|---|---|---|---|---|
| 304 | 3.05 | 3.01 | 3.03 | 3.02 | 3.01 | 3.00 |
| 342 | 3.00 | 3.01 | 3.02 | 3.01 | 3.04 | 3.03 |
| 380 | 3.01 | 3.00 | 3.00 | 2.98 | 3.02 | 3.03 |

TABLE II

Diametre of same six stents as above under an external Pressure of 40 mmHg (corresponding to human blood pressure)

| Number of cycles (millions) | Stent #1 | Stent #2 | Stent #3 | Stent #4 | Stent #5 | Stent #6 |
|---|---|---|---|---|---|---|
| 0 | 2.97 | 2.96 | 2.99 | 3.00 | 3.00 | 2.97 |
| 38 | 3.00 | 2.98 | 2.98 | 2.97 | 2.97 | 2.98 |
| 76 | 3.07 | 2.98 | 3.02 | 3.00 | 2.94 | 2.98 |
| 114 | 3.04 | 3.03 | 3.02 | 3.00 | 2.98 | 3.00 |
| 152 | 3.01 | 3.01 | 3.02 | 3.02 | 3.00 | 3.01 |
| 190 | 3.01 | 3.01 | 3.03 | 3.03 | 3.00 | 3.02 |
| 228 | 3.00 | 2.97 | 3.01 | 3.02 | 3.00 | 2.99 |
| 266 | 2.99 | 2.96 | 3.01 | 3.00 | 3.00 | 2.99 |
| 304 | 3.02 | 3.01 | 3.02 | 3.02 | 3.00 | 3.01 |
| 342 | 3.00 | 2.99 | 3.01 | 3.00 | 3.03 | 3.01 |
| 380 | 3.01 | 3.01 | 2.98 | 2.96 | 3.01 | 3.03 |

It can be seen that there is no significant difference of diameter after 380 millions cycles of fatigue tests, evidencing the exceptional mechanical resistance of the stents obtained according to the invention which is clearly unexpected.

EXAMPLE 3 OF THE INVENTION

Mechanical Piece Constituted by a Medical Body Implant, for Instance a Heart Valve having an Invention Ceramic Coating.

Using radio-frequency reactive magnetron deposition in customized PVD equipment, currently available on the particular market, it is deposited, similarly to example 1, on a thin steel or titanium valve-plate, a similar non porous nanometric layer of chromium for steel, furthermore a non porous nanometric layer of essentially pure titanium, to which follows a non porous nanometric layer of titanium nitride and a final non porous nanometric layer of titanium oxinitride. In case of using titanium as base material, the chromium layer has not to be applied. The successive metallic coating layers have thicknesses of 5 to 50 nm, preferentially of 10 to 15 nm; and the successive ceramic coating layers have a thickness of 10 to 40 nm.

The heart valve thus produced will display increased lifetime and extreme resistance to fatigue, which might result in scaling of the biological active coating. Furthermore, the cheap stainless steel 316L can be used; the three invention coatings set represent a perfect diffusion barrier against the elution of hazardous nickel from the steel substrate into the blood stream.

EXAMPLE 4 OF THE INVENTION

Mechanical Watch Regulatory Mechanisms

It is known that the regulatory mechanical watch mechanism, for instance anchor and escape wheel, are amongst the most solicited mechanical parts known to the engineers.

Accordingly, an important increase in lifetime or decrease in the maintenance cycle can be obtained if these mechanical parts could be coated with reliable, fatigue proof coatings.

4-1 According to the invention, a regulatory mechanical watch mechanism and can be coated with invention layers, as follows:

To the watch mechanism substrate it can be deposited a multiple layer nanostructured coating composed of an adhesion layer of chromium and titanium, the transient layer of carbon-nitride of titanium or of titaniumaluminide and a final layer of titanium nitride.

The coating can be produced, in order to satisfy the needs of most production by low temperature CVD using either inorganic or organometallic precursors at a temperature of 450 to 500° C. The gas mixture can be either ammoniac and titanium tetrachloride, with hydrogen as carrier and reduction gas or an organometallic precursor like tetarkis-(dimethylamido)titanium and tetrakis-(diethylamido)titanium, which together with ammoniac and hydrogen allows for rather lower deposition around 430 to 450° C.

4-2 According to a variant embodiment, an timekeeping mechanism could be coated with a layer or titanium of chromium or its alloys almost followed by a sandwich consisting of titanium nitride, titanium carbide and diamond like carbon (DLC), ensuring thus a maintenance free timekeeping mechanism.

EXAMPLE 5 OF THE INVENTION

A Body Joint Implant

A body joint implant like a hip implant or a knee implant can be coated with at least one non porous metallic adhesion layer of the invention and then with successive functional layers.

This functional layer is the optimization of the biological, medical, physical, chemical, requirements of the embodiments.

In tribological applications, the presence of at least one of a titanium nitride or of a hasnium nitride layer provides a very low coefficient of friction combined with excellent cohesion and strain-stress properties and fatigue properties of biological necessities as above described.

The invention can also be applied on a multitude of mechanical pieces and by way of example to flexible parts of pacemaker electrodes, syringes for medium and long term application in the human body; removable electronic hearing aids, etc.

The invention claimed is:

1. A stent having improved mechanical resistance, having a structure comprising a substrate, an essentially non porous metallic adhesion first coating layer of nanometric size, at least one essentially non porous ceramic barrier second coating layer of nanometric size of essentially stoichiometric titanium nitride over said adhesion first coating layer; and further comprising, over the second coating layer of titanium nitride, a surface third coating layer of nanometric size essentially non porous, essentially consisting of titanium oxide nitride; wherein said metallic adhesion first coating layer provides plastic deformability to the essentially non porous ceramic barrier second coating layer.

2. The stent of claim 1, wherein, the adhesion first coating layer is an essentially pure titanium nanometric, non porous coating layer.

3. The stent of claim 2, further comprising, over the third coating layer, a nanometric non porous fourth coating layer of essentially pure titanium, followed by a nanometric, non porous, ceramic fifth coating layer of titanium oxide nitride and an upper surface sixth coating layer of nanometric size essentially non porous, essentially consisting of titanium oxide nitride.

4. The stent of claim 1, wherein said titanium oxide nitride coating layer has a chemical formula $TiN_xO_y$, wherein x ranges between about 0.7 and about 1; and y is 1−x.

5. The stent of claim 1, further comprising, between two successive coating layers, a transient diffusion layer of nanometric size, essentially non porous, of a solid solution of at least one metal of the preceding layer and of at least one metal of the following layer.

6. The stent of claim 5, wherein the transient diffusion layer has a thickness ranging between 5 and 20% of the thickness of either one of adjacent successive coating layers.

7. The stent of claim 1, wherein the thickness of at least one or of each nanometric coating layer ranges between about 10 nanometers and 40 nanometers.

8. The stent of claim 1, wherein the essentially non porous metallic adhesion first coating layer has a thickness ranging between 5 and 20% of the thickness of the second or third coating layer.

9. The stent of claim 1, wherein the substrate is made of a metal or metal alloy selected from the group consisting of a steel, stainless steel; titanium, a titanium alloy; and a shape memory alloy.

10. The stent of claim 9, the essentially non porous metallic adhesion first coating layer is selected from the group consisting of an essentially pure chromium metal or chromium alloy, of a titanium metal or titanium alloy, and of a successive combination of both.

11. The stent of claim 1, wherein said substrate is a plastic substrate, selected from the group consisting of a polyester, a polyamide, a polyurethane, a polyethylene, a polytetrafluoroethylene, and a polycarbonate.

12. A stent having improved mechanical resistance, having a structure comprising:
   a substrate selected from the group consisting of a metal, a metal alloy, a stainless steel, titanium, a titanium alloy, and a shape memory alloy;
   an essentially non porous metallic adhesion first coating layer of nanometric size;
   at least one essentially non porous ceramic barrier second coating layer of nanometric size of essentially stoichiometric titanium nitride over said adhesion first coating layer; and
   further comprising, over the second coating layer of titanium nitride, a surface third coating layer of nanometric size essentially non porous, essentially consisting of titanium oxide nitride;
   wherein said metallic adhesion first coating layer provides plastic deformability to the essentially non porous ceramic barrier second coating layer.

13. The stent of claim 12, further comprising, between two successive coating layers, a transient diffusion layer of nanometric size, essentially non porous, of a solid solution of at least one metal of the preceding layer and of at least one metal of the following layer.

* * * * *